United States Patent [19]

King et al.

[11] Patent Number: 5,338,303
[45] Date of Patent: Aug. 16, 1994

[54] SAFETY SYRINGES

[75] Inventors: Richard J. King, Jupiter, Fla.; John R. Gordon, Santa Monica, Calif.

[73] Assignee: Design and Engineering Associates, Jupiter, Fla.

[21] Appl. No.: 940,928

[22] Filed: Sep. 8, 1992

[51] Int. Cl.$^5$ .............................................. A61M 5/00
[52] U.S. Cl. .................................. 604/110; 604/192; 604/198
[58] Field of Search ............... 604/110, 198, 187, 192, 604/263

[56] References Cited

U.S. PATENT DOCUMENTS

| | | | |
|---|---|---|---|
| Re. 33,585 | 5/1991 | Haber et al. | 604/198 |
| Re. 34,045 | 8/1992 | McFarland | 604/198 |
| 3,669,111 | 6/1972 | Dubner | 128/128 P |
| 4,356,822 | 11/1982 | Winstead-Hall | 128/215 |
| 4,710,170 | 12/1987 | Haber et al. | 604/110 |
| 4,717,386 | 1/1988 | Simmons | 604/192 |
| 4,747,830 | 5/1988 | Gloyer et al. | 604/110 |
| 4,758,231 | 4/1988 | Haber et al. | 604/198 |
| 4,767,413 | 8/1988 | Haber et al. | 604/198 |
| 4,770,665 | 9/1988 | Haber et al. | 604/110 |
| 4,781,701 | 11/1988 | Geprags | 604/240 |
| 4,786,281 | 11/1988 | Valentini et al. | 604/256 |
| 4,790,827 | 12/1988 | Haber et al. | 604/198 |
| 4,804,370 | 2/1989 | Haber et al. | 604/195 |
| 4,808,169 | 2/1989 | Haber et al. | 604/195 |
| 4,820,275 | 4/1989 | Haber et al. | 604/198 |
| 4,826,484 | 5/1989 | Haber et al. | 604/110 |
| 4,826,489 | 5/1989 | Haber et al. | 604/198 |
| 4,834,717 | 5/1989 | Haber et al. | 604/193 |
| 4,838,870 | 6/1989 | Haber et al. | 604/187 |
| 4,842,587 | 6/1989 | Poncy | 604/198 |
| 4,861,338 | 8/1989 | Mathiesen et al. | 604/110 |
| 4,874,384 | 10/1989 | Nunez | 604/198 |
| 4,892,523 | 1/1990 | Haber et al. | 604/198 |
| 4,915,702 | 4/1990 | Haber | 604/198 |
| 4,927,018 | 5/1990 | Yang et al. | 604/110 X |
| 4,927,417 | 5/1990 | Moncada et al. | 604/198 |
| 4,950,241 | 8/1990 | Ranford | 604/110 |
| 4,950,242 | 8/1990 | Alvarez | 604/110 |
| 4,958,622 | 9/1990 | Selenke | 128/765 |
| 4,961,730 | 10/1990 | Poncy | 604/198 |
| 4,969,454 | 11/1990 | Servello | 606/185 |
| 4,982,843 | 1/1991 | Jones | 206/366 |
| 4,986,813 | 1/1991 | Blake, III et al. | 604/110 |
| 4,986,817 | 1/1991 | Code | 604/192 |
| 4,994,723 | 7/1991 | Haber et al. | 604/110 |
| 4,998,920 | 3/1991 | Johnson | 604/198 |
| 5,000,736 | 3/1991 | Kaufhold, Jr. et al. | 604/110 |
| 5,000,738 | 3/1991 | LaVallo et al. | 604/110 |
| 5,002,533 | 3/1991 | Jullien | 604/110 |
| 5,013,299 | 5/1991 | Clark | 604/114 |
| 5,019,051 | 5/1991 | Hake | 604/263 X |
| 5,035,703 | 7/1991 | Baskas | 604/167 |
| 5,047,017 | 9/1991 | Koska | 604/110 |
| 5,053,018 | 10/1991 | Talonn et al. | 604/198 |
| 5,066,281 | 11/1991 | Stevenson-Michener | 604/110 |
| 5,067,948 | 11/1991 | Haber et al. | 604/213 |
| 5,084,018 | 1/1992 | Tsao | 604/110 |
| 5,084,019 | 1/1992 | Gartz | 604/110 |
| 5,085,338 | 2/1992 | Inagaki | 220/254 |
| 5,102,083 | 4/1992 | Baskas | 248/223.4 |
| 5,106,380 | 4/1992 | Lobello | 604/198 |
| 5,108,378 | 4/1992 | Firth et al. | 604/192 |
| 5,122,117 | 6/1992 | Haber et al. | 604/90 |
| 5,125,836 | 7/1992 | Dragan et al. | 433/90 |
| 5,125,898 | 6/1992 | Kaufhold, Jr. et al. | 604/110 |
| 5,201,721 | 4/1993 | Lee et al. | 604/198 |

FOREIGN PATENT DOCUMENTS 8806463 9/1988 World Int. Prop. O. .......... 604/192

OTHER PUBLICATIONS

Jagger et al., New England Journal of Medicine, 319: 284–288 (Aug. 4, 1988).

*Primary Examiner*—John D. Yasko
*Attorney, Agent, or Firm*—Ernest V. Linek

[57] ABSTRACT

The improvements in shielded safety syringes described herein provide a safe and simple mechanism to reduce and preferably eliminate accidental needle-stick injuries. The improvements described herein further provide a safe and simple means to prevent unauthorized reuse of the syringe. The improved syringe of the present invention locks the needle assembly in the shield member after use, preventing reuse and accidental needle-stick injuries.

8 Claims, 3 Drawing Sheets

SAFETY SYRINGES

BACKGROUND OF THE INVENTION

The medical or veterinary use of syringes and other needle bearing devices involves a well-defined risk of accidental contact with the needle, a so-called needle-stick injury. In many cases (e.g., HIV), such needle-stick injuries can have deadly implications. In one published needle-stick injury study, the characteristics of needle-stick injuries caused by various needle bearing devices was analyzed. Of 326 injuries occurring over a ten month period (almost 33 incidents per month), disposable syringes accounted for 35 percent, all intravenous devices accounted for 35 percent, prefilled cartridge syringes accounted for 12 percent, phlebotomy needles accounted for 5 percent, and other devices accounted for 13 percent thereof. See, Jagger et al., *New England Journal of Medicine*, 319: 284–288 (1988).

One commercially available disposable syringe is illustrated in FIGS. 1A–1F. This syringe is Becton-Dickinson Company's Plastipak ® Luer-Lok ® syringe. As illustrated, plastic non-shielded disposable syringes generally have few parts. The plastic plunger 10 is provided with a rubber plunger tip 12 and in combination these elements form the plunger assembly which creates the necessary pressure to draw and/or expel fluids into or from the syringe barrel 14. The tip of the plastic syringe barrel 15 is typically shaped to accept a needle and hub combination 16, sometimes referred to as the needle assembly. In many disposable syringes the fit of the needle assembly on the tip of the syringe barrel is by friction. In other cases, some locking means may be employed, e.g., twist action, screw action, etc. Finally, in most disposable plastic syringes commercially available today, the needle assembly is further provided with a plastic needle guard 18 which fits over the needle prior to use, and which may be employed after use to prevent accidental needle-stick injuries after the disposed of syringe. In most cases, the attachment of the needle guard 18 over the needle assembly is by friction fit, but other attachment means may also be employed, e.g., twist action, snap lock, screw action, and the like.

In syringes of the FIGS. 1A–1F type, there is an obvious needle-stick danger associated with the act of reattaching the needle guard to a used needle, and this why such syringes are becoming less and less popular. As reported by Jagger et al., supra, the recapping of disposable syringes was the most common mechanism of needle-stick injuries for such devices. Recapping accidents typically occurred in three ways; (1) the cap was missed entirely; (2) the needle pierced a cap that was too short; and (3) the cap fell off of the needle after disposal.

The U.S. Department of Labor, through the Occupational Safety and Health Administration (OSHA) in compliance directive CPL 2-2.44B, Enforcement Procedures for Occupational Exposure to Hepatitis B Virus and Human Immunodeficiency Virus, expressly prohibits the recapping of used needles and other sharp instruments by hand.

Improvements in syringe designs, particularly safety syringes where the syringe itself is provided with means specifically designed to reduce or eliminate accidental needle-sticks and/or unauthorized reuse of the syringe, are thus in great demand.

Two safety syringes currently being marketed are the Becton-Dickinson Co. Safety-Lok TM syringe and the Sherwood Medical Co. Monoject ® safety syringe. These syringes are both sleeve-type safety syringes, wherein a sleeve located around the syringe barrel, can be extended over the needle area to prevent accidental needle-stick injuries.

In each case, the sleeve is slidably attached to the syringe barrel, with a locking means at the needle end thereof. Before use, the sleeve is positioned rearwardly, so that the needle is exposed and available for use. After use, and prior to safe disposal, the sleeve is extended in a forward manner, over the exposed needle, and it is locked in place. While these two devices solve several of the needle-stick problems presently faced by users of such devices, they do not prevent the reuse of the syringe by others, nor do they provide all of the other advantages associated with the improvements in such designs as taught herein.

These two commercially available syringes are illustrated in FIGS. 2A–2I and 3A–3K attached hereto.

Many of the components employed in the FIGS. 2A–2I device are also present in the FIGS. 1A–1F syringe, since the two syringes originate from a common source, the Becton-Dickinson Company (B-D). The FIGS. 2A–2I syringe is B-D's Safety-Lok syringe. As in the FIGS. 1A–1F syringe, the FIGS. 2A–2F plunger 10 is provided with a plunger tip 12, and the syringe further includes a barrel 14. As before, the tip of the syringe barrel 15 is shaped to accept the needle and hub combination 16, sometimes referred to as the needle assembly. The needle assembly 16 is further provided with a needle guard 18 which sits over the needle prior to use. As in the previously described syringe, the attachment of the needle guard 18 over the needle assembly is by friction fit. This needle guard however, is not intended to be reused.

The unique components of the FIGS. 2A–2I syringe are the barrel locking ring 20, which fits over the tip of the syringe barrel 15 and may be used to lock the needle assembly 16 thereto, and the needle shield 22, which slidably fits around the periphery of the syringe barrel 14 and which has locking means 24 at the rear end thereof.

When positioned over the periphery of the syringe barrel 14, the shield 22, in its use position is essentially contiguous with the barrel 14, and the needle assembly is substantially exposed. After use, the shield 22 is pushed forward, over the needle assembly 14 until the locking means 24 mates with locking ring 20 located at the tip of the barrel. In this position, the syringe may be safely disposed of.

One drawback of this design is that the locking mechanism is not permanent, i.e., the locked shield may readily be unlocked, and the syringe could be reused by an unauthorized party. More importantly, should the safety shield become disengaged before or after disposal, the risk of accidental needle-stick injury is no different than with the unshielded syringe design. The syringe design of the present invention attempts to solve these deficiencies.

Another commercially available shielded syringe is illustrated in FIGS. 3A–3K. This syringe is available as the Monoject ® safety syringe from the Sherwood Medical Company. As in the previously described syringes, many of the components are common including the plunger 10, which is provided with a plunger tip 12, the syringe barrel 14 and needle assembly 16, and finally the needle guard 18. As with the previously described shielded syringe, the needle assembly is further provided with a needle guard 18 which sits over the needle prior to use. As in the previously described syringes, the attachment of the needle guard 18 over the needle assembly is by friction fit, and as in the previous shielded design, this needle guard is not intended to be reused.

The unique components of the FIGS. 3A–3K syringe are akin to those used in B-D's Safety-Lok syringe (FIGS. 2A–2I) and include a barrel locking ring 20, which fits over the tip of the syringe barrel 15 and may be used to lock the needle assembly 16 thereto, a slidable needle shield 22, which fits around the periphery of the syringe barrel 14 and which has locking means 24 at the rear end thereof. Finally, the front end of the safety shield, there is provided a restrictive collar 25, which effectively prevents finger contact with the needle when the safety shield is extended.

When positioned over the periphery of the syringe barrel 14, the shield 22, in its use position is essentially contiguous with the barrel 14, and the needle assembly is substantially exposed. Unlike the B-D Safety-Lok ™ safety syringe, the Monoject ® safety syringe further includes positive shield stops (not shown) in both the extended and retracted positions to prevent accidental movement of the shield while drawing medication, giving an injection, transporting the filled syringe, or discarding the used syringe. After use, the shield 22 is pushed forward, over the needle assembly 14 until the locking means 24 mates with locking ring 20 located at the tip of the barrel. A two-step locking mechanism is employed in the Monoject ® safety syringe. In the first position, the shield may be retracted. In the second position, the stop mechanism is designed so that it cannot be overridden, thereby preventing unauthorized reuse thereof. When locked in this second position, the syringe may be safely disposed of.

One drawback in the design of the Monoject ® syringe is that the locking mechanism must be securely fixed in the second position prior to disposal. This may not always take place, thereby giving the unauthorized user an opportunity to reuse the syringe. In addition, given enough force, the locking mechanism presently employed on the Monoject ® syringe can be overridden, enabling an unauthorized user access to the syringe. If the shield becomes unlocked during or after proper disposal, the risk of accidental needle-stick injury is no different than with the unshielded syringe design. The syringe design of the present invention attempts to resolve these deficiencies.

Other unique syringe designs intended to reduce accidental needle-strike incidents are shown in the following U.S. Patents, the disclosures of which are hereby incorporated herein by reference:

U.S. Pat. No. Re. 33,585, which provides a shielded safety syringe; U.S. Pat. No. 5,125,898, which is directed to a disposable syringe with automatic needle retraction; U.S. Pat. No. 5,122,117, which teaches and claims a component mixing syringe; U.S. Pat. No. 5,108,378, directed to a disposable self-shielding hypodermic syringe; U.S. Pat. No. 5,106,380, which claims a shielded syringe; U.S. Pat. No. 5,084,019, which claims a syringe with means to destroy and safely store the cannula; U.S. Pat. No. 5,084,018, claiming safety syringes; U.S. Pat. No. 5,066,281, directed to a disposable syringe apparatus with retractable needle, locking device and cap device; U.S. Pat. No. 5,047,017, directed to a syringe which will render itself useless after one drug shot and which is tamperproof; U.S. Pat. No. 5,035,703, which claims a disposable syringe needle and scalpel holder; U.S. Pat. No. 5,013,299, which claims a syringe resheathing device; U.S. Pat. No. 5,002,533, directed to a syringe guard apparatus; U.S. Pat. No. 5,000,738, which claims a protective syringe with frangible barrel; U.S. Pat. No. 5,000,736, which is directed to a disposable syringe with automatic needle retraction; U.S. Pat. No. 4,986,817, which claims a hypodermic syringe sheath holder and needle guide; U.S. Pat. No. 4,986,813, which claims a disposable hypodermic syringe; U.S. Pat. No. 4,969,454, which claims an emergency percutaneous cricothyrotomy device; U.S. Pat. No. 4,958,622, which claims a hypodermic syringe for taking and transporting a specimen; U.S. Pat. No. 4,950,242, which is directed to a hypodermic needle cover and assembly therewith; U.S. Pat. No. 4,950,241, which claims a disposable syringe; U.S. Pat. No. 4,944,723, which describes a universal disposable safety syringe system; U.S. Pat. No. 4,915,702. which claims a shielded safety syringe; U.S. Pat. No. 4,904,243, which is directed to a device for self-administration of drugs or the like; U.S. Pat. No. 4,894,054, which claims a preloaded automatic disposable syringe; U.S. Pat. No. 4,892,523, which is directed to a shielded safety syringe; U.S. Pat. No. 4,861,338, which claims a safety syringe; U.S. Pat. No. 4,838,870, which is directed to a removable needle attachment having a detachable needle; U.S. Pat. No. 4,834,717, which claims a disposable, pre-sterilizable syringe for a prefilled medication cartridge; U.S. Pat. No. 4,826,489, directed to a disposable safety syringe having means for retracting its needle cannula into its medication cartridge; U.S. Pat. No. 4,826,484, which claims a disease control syringe having a retractable needle; U.S. Pat. No. 4,820,275, which is directed to a retractable needle syringe with integral spring; U.S. Pat. No. 4,808,169, which claims a disposable safety syringe having means for retracting its needle cannula into its medication cartridge; U.S. Pat. No. 4,804,370, which is directed to a disease control syringe having a retractable needle; U.S. Pat. No. 4,790,827, which claims a shielded safety syringe; U.S. Pat. No. 4,786,281, which is directed to a device for connecting one end of a liquid medicament delivery cannula to an apparatus for connecting a syringe to a vial containing the medicament; U.S. Pat. No. 4,781,701, which claims a syringe for medical purposes; U.S. Pat. No. 4,770,655, which is directed to a disease control syringe having a retractable needle; U.S. Pat. No. 4,767,413, which claims a dental syringe having an automatically retractable needle; U.S. Pat. No. 4,758,231, directed to a shielded safety syringe; U.S. Pat. No. 4,747,830, which claims an anti-stick contagion free disposable hypodermic safety syringe; U.S. Pat. No. 4,717,386, which is directed to a safety device for a needle; U.S. Pat. No. 4,710,170, which claims an anti-needle strike and anti-drug abuse syringe; U.S. Pat. No. 4,356,822, which claims a syringe assembly; U.S. Pat. No. 4,186,783, which is entitled Chemical injector; U.S. Pat. No. 3,727,613, entitled Safety Catheter Placement Assembly; and U.S. Pat. No. 3,669,111 entitled Automatic Retracting Hypodermic Syringe, among others.

Another safety syringe design is shown in copending application Ser. No. 07/787,915, filed Nov. 6, 1991, now U.S. Pat. No. 5,188,601. The disclosure of this application is hereby incorporated herein by reference.

The recitation of patented safety syringes provided above is not intended as being a complete listing of all safety syringes patented in the United States over the last twenty (20) years. It is merely provided to show the great interest in this art area, and to provide a basis of the numerous designs of such syringes wherein the improvements of the type described and claimed herein can be employed.

SUMMARY OF THE INVENTION

The improvements in safety syringes described herein provide a safe and simple mechanism to reduce and preferably eliminate accidental needle-stick injuries, not only by the intended users of the syringe, but more importantly by persons who may come into contact with the syringe after or during the disposal thereof, e.g., sanitation personnel and the like. In addition, the improvements described herein further provide a safe and simple means to prevent unauthorized reuse of the syringe.

The present invention is thus directed to improvements in slidable sleeve type safety syringes, such as those commercially available from the Sherwood Medical Co. as the Monoject ® safety syringe and/or those syringes available from the Becton-Dickinson Co. as the Safety-Lok TM syringe. In each of these commercially available syringes, the needle assembly comprises a Luer-Lok mechanism wherein the needle assembly consists of a cannula and a female luer portion and the barrel terminates in a matching male luer portion. The safety shield in each case fits over the syringe barrel and can be slidably positioned over the needle assembly. Locking means are provided at one end of the safety shield and on the barrel, so that when engaged, they secure the needle shield over the needle assembly, e.g., when use of the syringe is completed. However, in each design, the locking means is at least partially releasable, and if an unauthorized person obtained the used needle, it could be reused. Also, if the locking means accidentally became disengaged, a potential needle-stick injury could occur.

The present invention solves the disadvantages associated with this type of safety syringe by only a slight modification of the overall general design described above. The improvement of this invention inheres primarily in the safety shield and needle hub designs. In this invention, the safety shield is constructed not only to fit around the syringe barrel, as in the previously known safety syringes of this type, but it is further provided with means, e.g., two or more stations, suitable for locking onto a modified outer hub of the needle assembly, such that instead of locking to the barrel so as to cover the needle, the needle assembly itself is locked into the sleeve.

One preferred modification to the outer hub of the needle assembly is a rigid collar, designed to snap-fit into two of more locking stations provided in the safety shield. In the currently most preferred embodiment of this invention, the rigidity of the needle assembly collar prevents the reuse of the syringe, since once engaged in the shield locking stations, it cannot be disengaged.

Other modifications and locking mechanisms will be apparent to the skilled artisan, and are deemed part of this invention if they cause a locking between the needle assembly and the safety shield. The prior art devices typically include a locking of the shield on the syringe barrel.

The advantage of this design will be apparent upon consideration of the details of this invention which are provided below.

DETAILED DESCRIPTION OF THE PREFERRED EMBODIMENTS

Figure 1:
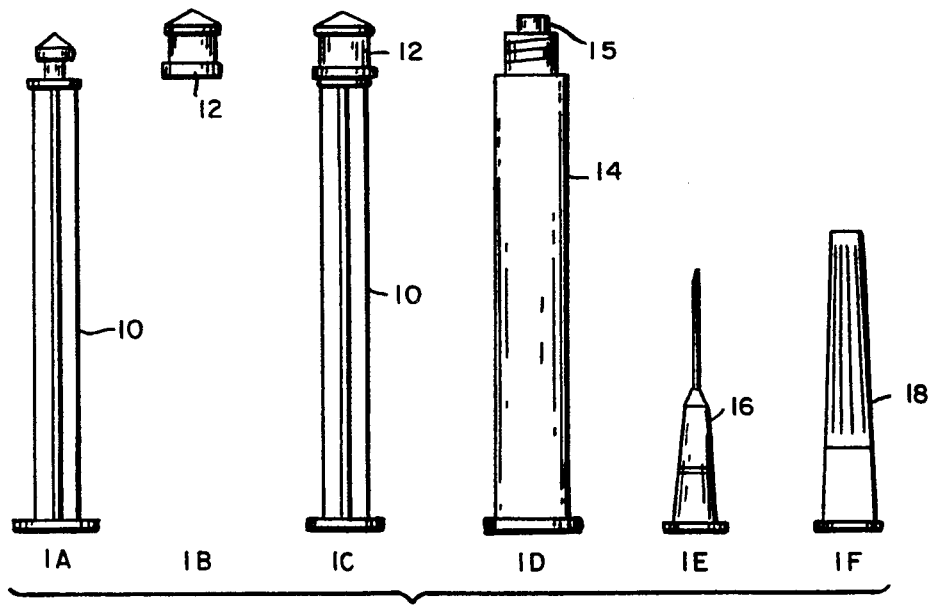
FIGS. 1A-1F are plan views illustrating in separate pieces, the components of one commercially available standard disposable syringe, the Becton-Dickinson (B-D) Company's Plastipak ® Luer-Lok ® syringe.

In the prior art shielded syringe devices discussed above and illustrated in the Figures, the outer hub of the needle is generally a simple structure. As in the other prior art devices discussed, it typically includes the centrally situated hollow cannula or needle and has a tapered or conical shape, sometimes ending with a flat ridge at the mounting end. If a needle guard is included with the syringe (as in three illustrated prior art devices) the periphery of the hub may include means for retaining such a guard in a friction or locking fit manner. The interior, or female portion of the luer is shaped so as to fit snugly and in a vacuum sealed manner, with the male luer on the barrel tip, so as to provide the necessary means to draw or deliver liquids into or out of the syringe.

In the present invention, the outer hub of the needle assembly (or luer) is further provided with an outwardly projecting collar, which will snap fit with locking means therefor provided in the rearward portion of the safety shield. Thus, in the present invention, when the safety shield is pushed forward over the needle assembly (e.g., after use) to a point where it locks with the collar thereon, the needle may safely be discarded, as it is no longer usable.

Moreover, if the luer assembly of the syringe is designed to be detachable, e.g., through a twist-off rotation, a friction release, or the like, after the safety shield has engaged the needle hub, the syringe may simply be twisted, pushed or pulled apart, allowing the user to discard two individually safe components—the barrel and plunger combination and the needle assembly, which is locked securely in the safety shield, from which it will be virtually impossible to remove for reuse, and needle-stick injuries therefrom will be essentially eliminated.

Thus, the present invention is directed to a new design of shielded safety syringes, wherein the shield is used to secure and protect the needle assembly after use, and in an especially preferred embodiment, the shielded needle assembly is disposed of separately from the body of the syringe. Thus, two separate pieces, each useless per se are safely disposed of, eliminating the potential of accidental needle-stick injuries to sanitary personnel or others who may come into contact with the disposed of syringe, the reuse of which is impossible. In addition, to further prevent possible reassembly and reuse of the discarded syringe pieces, a break-off plunger assembly may be included, so that three unusable pieces are finally disposed of.

As shown in FIGS. 4A–4I, the shielded safety syringe of the present invention represents a significant departure from the previous commercial designs of such syringes. A shown in this series of Figures, the syringe comprises many of the same components used in the previously discussed prior art devices, including plastic plunger 10, which is provided with a rubber plunger tip 12, plastic syringe barrel 14 and needle assembly 16. Optionally, the syringe may include other previously used component parts, including needle guard 18, and restrictive collar 25.

One readily apparent difference between the prior art shielded syringes and this invention is the design of the needle assembly 16. As particularly shown in FIGS. 5A, 5B, and 5C, the needle assembly of this invention includes a collar member 17 which flares outwardly from the hub of the needle assembly. This rigid collar member may be readily formed during the manufacture of the hub, by any process available to the skilled artisan, e.g., molding, machining, etc.

Figure 2:
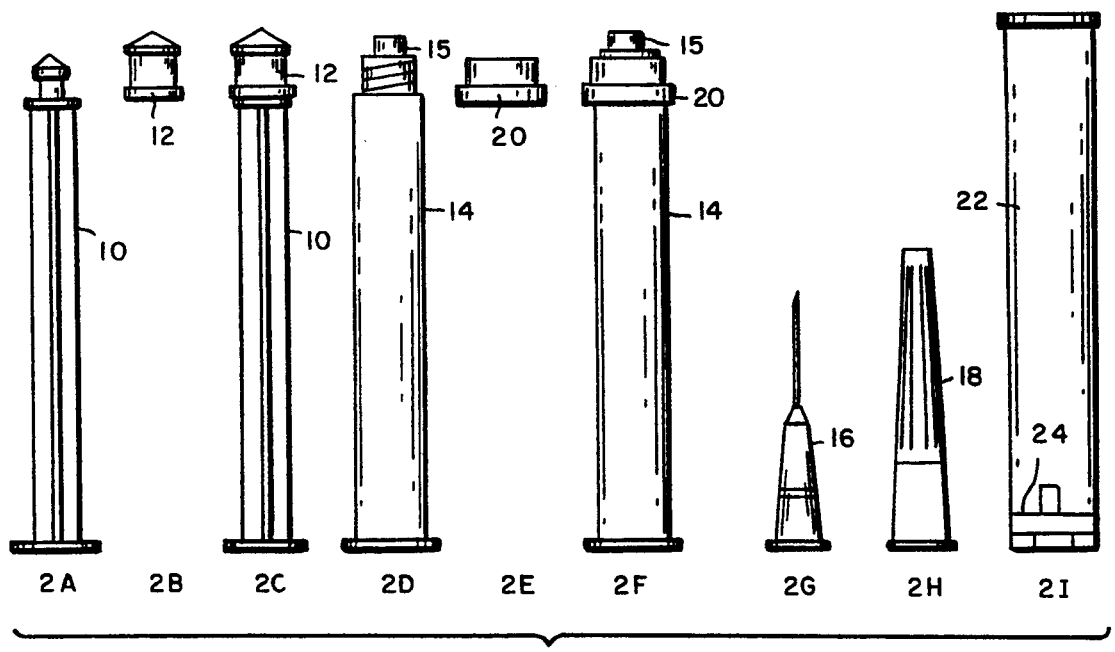
FIGS. 2A-2I are plan views illustrating in separate pieces, the components of one commercially available shielded safety syringe, the Becton-Dickinson (B-D) Company's Safety-Lok TM syringe.
Figure 3:
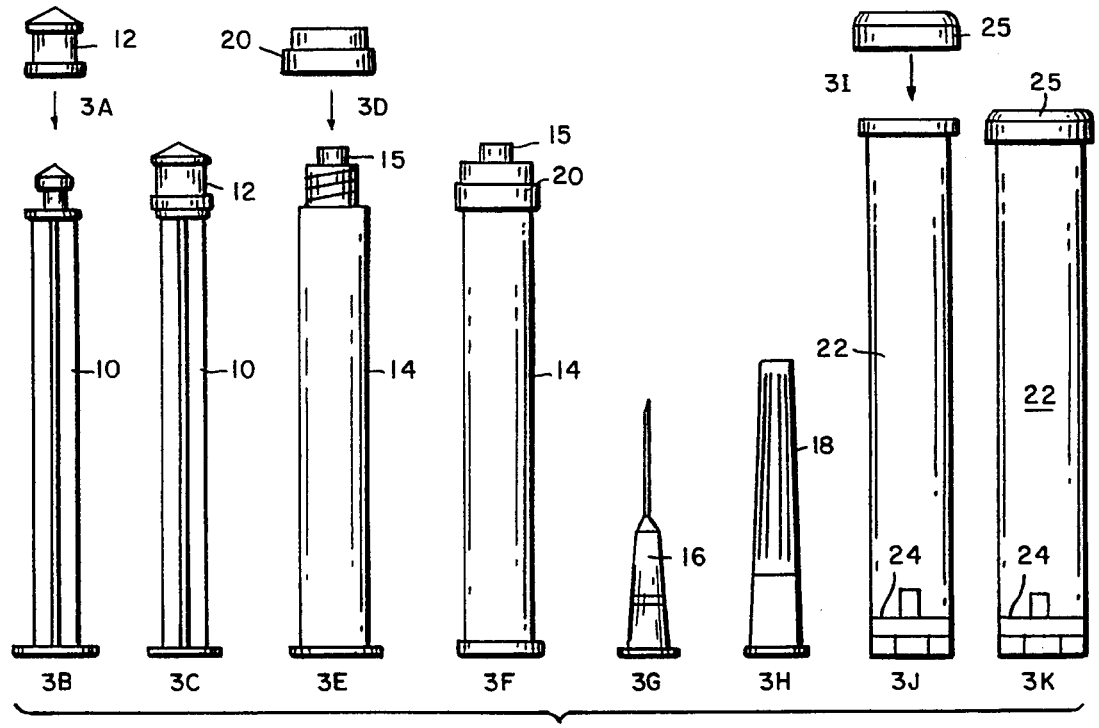
FIGS. 3A-3K are plan views illustrating in separate pieces, the standard components of another commercially available shielded safety syringe, the Sherwood Medical Company's Monoject ® safety syringe.
Figure 4:
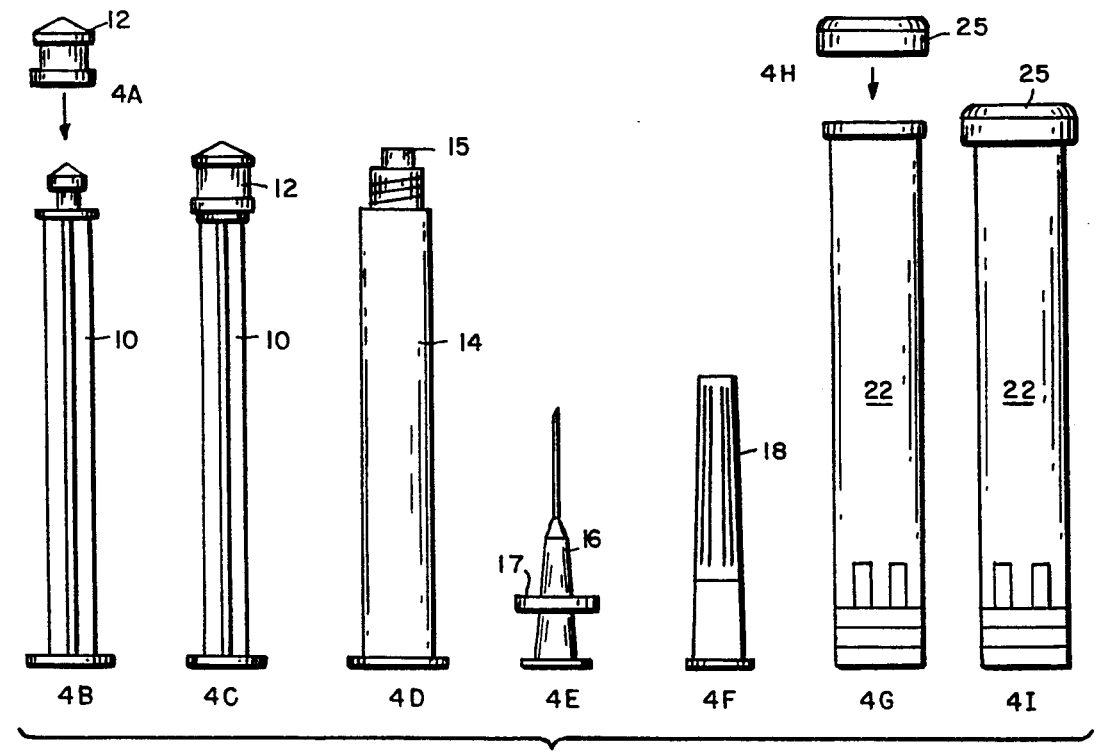
FIGS. 4A-4I are plan views illustrating in separate pieces, the components (standard and optional) of one embodiment of the syringe of the present invention.
Figure 5A:
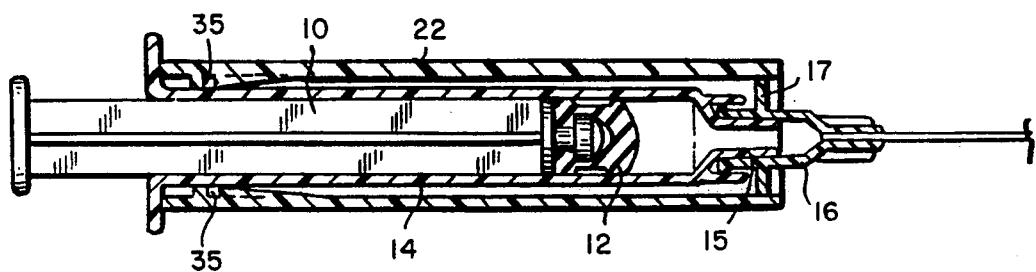
FIGS. 5A-5D are sectional views illustrating one embodiment of the improved shield-type safety syringe of the present invention.
Figure 5B:
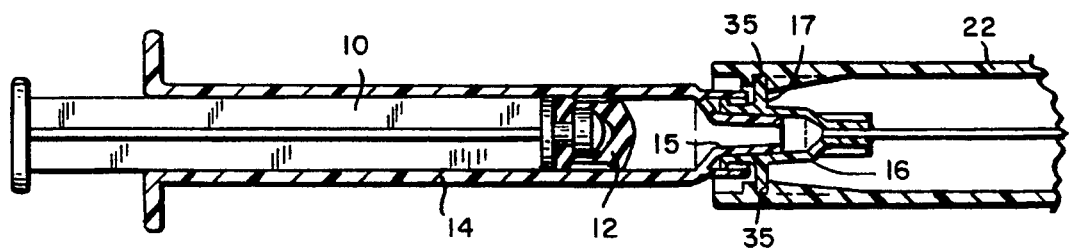

As shown in FIGS. 5A and 5B, one improvement of this syringe embodiment over the prior art is the elimination of the barrel locking ring 20 (e.g., in FIGS. 2E and 3D), which in the prior art were used as the locking point of the safety shield over the needle assembly. In one preferred embodiment of this invention, a Luer-Lok mechanism, akin to that employed in the Plastipak ® syringe, is relied upon to maintain contact between the needle assembly 16 and the syringe tip 15. That way, by simple rotation, the needle may be removed and disposed of in a safe and effective manner.

As shown in FIG. 5A, in the use position, the slidable safety shield 22 is substantially coextensive over the length of the syringe barrel 14, and the needle assembly 16 is fully exposed, ready for filling and/or injection.

Figure 5D:
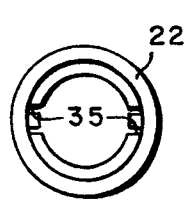
Figure 5C:
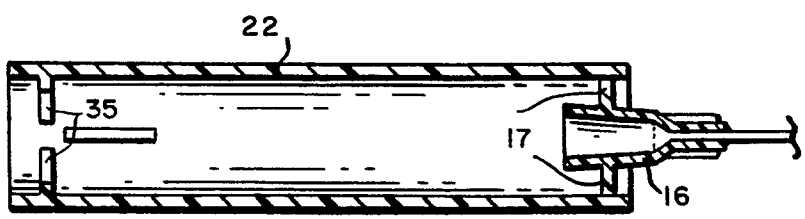

Referring to FIGS. 5C and 5D, it will be noted that the slidable needle shield 22 has an internal diameter substantially the same as the outside diameter of the rigid collar 17 on the needle hub. There is sufficient difference in size to allow the needle shield 22 to slide easily over the collar 17, but at the back end of shield 22, there are two or more locking stations 35, into which collar 17 will fit, thereby locking the needle assembly deep within the extended shield 22—safely away from the potential of a needle-stick injury. The rigidity of collar 17 is greater than the rigidity of the shield 22, such that as gentle force is applied to engage the shield over the needle collar 17, the shield expands slightly outward. Once the collar 17 meets the locking stations 35, the shield snaps back to its original configuration, permanently locking the needle assembly therein.

Once the safety shield 22 and collar 17 on the needle assembly 16 have been securely locked in place, e.g., as illustrated in FIG. 5B, the engagement mechanism (e.g., Luer lock, frictional fit, etc.) between the syringe barrel tip 15 and the needle assembly 16 may be disengaged, e.g., by rotation, pushing, pulling, etc. The two sections of the used syringe can then be safely disposed of, i.e., the barrel and plunger assembly, and the safety shielded needle assembly. Advantageously to prevent reuse of the otherwise useful plunger 10 and barrel 14 combination, the plunger 10 may be provided with break-off means, e.g., a score line or the like (not shown) such that prior to disposal thereof, a portion of the plunger is broken off, leaving a part thereof in the syringe barrel, making the disposed pieces entirely useless.

As illustrated in FIG. 5B, the entire assembly could be disposed of without separation of the shielded needle assembly and the syringe/plunger combination. As described above, however, this is not the most preferred disposal route since the bulk of the disposed syringe would be unnecessarily large. The design of the present invention allows for the easy and safe separation of the shielded needle assembly from the barrel/plunger combination. This nearly cuts the length of the disposed material in half, reducing even further the possibility of any disposal problems.

If desired, the front end of the safety shield may be provided with a restrictive collar (not shown) which would serve to further preclude the possibility of finger contact with the needle locked within the safety shield, e.g., either before, during or after the disposal thereof.

Figure 6:
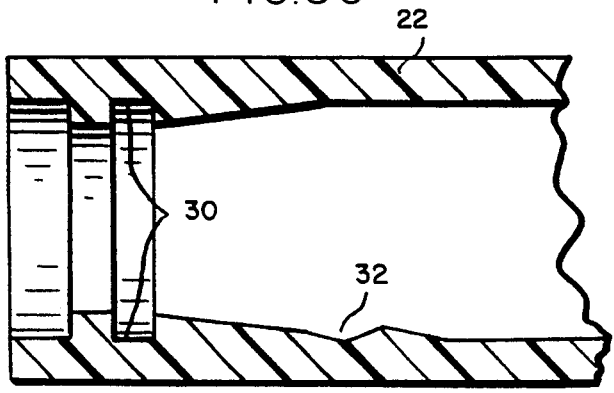
FIG. 6 is a sectional view illustrating an alternative sleeve embodiment with two stations or locking means, one of which is a temporary stop for the shield.

FIG. 6 illustrates another embodiment of the safety shield 22 of the present invention, showing locking means 30 into which the collar 17 on the needle assembly 16 will fit for safe disposal. In addition thereto, an intermediate locking position 32 is shown. This position would be used for transport of the syringe in a safe manner, with the safety shield 22 positioned over the needle, but in a readily unlockable mode, e.g., before giving an injection. In this position, the safety shield 22 can easily be retracted to expose the needle. After use, the shield 22 would be extended fully whereby collar 17 would permanently engage locking member 30, and after separation of the needle assembly from the syringe barrel (if desired) the two pieces (or three if a break-off plunger is used) can be safely disposed of.

The disposable shielded safety syringe of the present invention may be prepared from any of the currently available plastic materials commonly employed in making disposable syringes. These are generally transparent or clear so that the contents can be readily seen. Likewise the safety shield should be prepared from a clear or transparent plastic material. Molding and/or machining processes for the formation of the various parts described herein are well within the ordinary skill of the artisans in this field, and they need not be presented in any detail herein. If a disposable plunger is to be included in the syringe, the plastic should be capable of breaking without undue exertion of strength or time. Many plastics used in disposable syringes are nearly unbreakable, and while these are preferred for the barrel and the safety shield, they are not readily usable for a break-off plunger. The skilled artisan will readily be capable of selecting appropriate materials in view of this disclosure.

As used herein, the term "syringe" is intended to include all devices which include an exposed needle for the injection and/or removal of fluid material to or from a patient, whether human or animal. All syringes thus defined can be modified to have a safety shield which locks onto the needle assembly to prevent accidental needle-stick injuries.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. In a disposable shielded safety syringe comprising a syringe barrel, a slidable plunger assembly therein, and a needle assembly at one end thereof, with a safety shield surrounding at least a portion of the periphery of the syringe barrel; the improvement comprising:

opposing locking means, one at the rearward segment of the safety shield and another on the needle assembly, wherein the locking means on the needle assembly comprises an annular rigid collar member connected to and projecting outwardly from the needle hub, whereby interaction between the opposing locking means causes the extended safety shield to engage and lock the needle assembly; and wherein the locking means on the safety shield comprise a plurality of locking stations extending into the inner surface of the sleeve.

2. In a disposable shielded safety syringe comprising a syringe barrel, a slidable plunger assembly therein, and a needle assembly at one end thereof, with a safety shield surrounding the periphery of the syringe barrel; the improvement comprising:

at least two locking stations at the rearward segment of the safety shield, which locking stations are capable of locking on to a locking member on the needle assembly, wherein the locking member on the needle assembly consists of an annular rigid collar member connected to and projecting outwardly from the needle hub, whereby interaction of the shield locking stations and the rigid collar causes the extended safety shield to engage and lock the needle assembly.

3. The disposable shielded safety syringe of claim 2, wherein the locking member on the needle assembly and the locking stations on the shield form a permanent combination, whereby they cannot become disengaged after locking together.

4. The disposable shielded safety syringe of claim 2, wherein the locking member on the needle assembly is integral with the hub of the needle assembly.

5. The disposable shielded safety syringe of claim 4, wherein the collar member has an outer diameter substantially equal to the inner diameter of the safety shield.

6. The disposable shielded safety syringe of claim 2, wherein the safety shield further includes at least one temporary stop rib on the inner surface, thereby allowing safe transport of the syringe with the needle covered in a temporary manner.

7. The disposable shielded safety syringe of claim 2, which further comprises a break-off plunger.

8. The disposable shielded safety syringe of claim 2, wherein the safety shield further comprises a restrictive collar member at the forward end thereof, thereby preventing finger contact with the needle surrounded thereby.

* * * * *